US00PP19273P3

(12) United States Plant Patent
Goffreda et al.

(10) Patent No.: US PP19,273 P3
(45) Date of Patent: Sep. 30, 2008

(54) PEACH TREE NAMED 'NJF18'

(50) Latin Name: *Prunus persica*
Varietal Denomination: NJF18

(75) Inventors: Joseph C. Goffreda, Manalapan, NJ (US); Anna M. Voordeckers, East Windsor, NJ (US)

(73) Assignee: Rutgers The State University, New Brunswick, NJ (US)

( * ) Notice: Subject to any disclaimer, the term of this patent is extended or adjusted under 35 U.S.C. 154(b) by 31 days.

(21) Appl. No.: 11/707,179

(22) Filed: Feb. 13, 2007

(65) Prior Publication Data

US 2008/0196129 P1 Aug. 14, 2008

(51) Int. Cl.
*A01H 5/00* (2006.01)

(52) U.S. Cl. ..... Plt./197

(58) Field of Classification Search ..... Plt./197
See application file for complete search history.

*Primary Examiner*—Kent L Bell
(74) *Attorney, Agent, or Firm*—James A. Lucas; Driggs, Hogg, Daugherty & Del Zoppo

(57) ABSTRACT

A new and distinct peach variety of *Prunus persica* named 'NJF18' is provided. This variety is distinguished from other peach varieties by its unique combination of showy flowers that are medium in width, flat fruit that ripen in early midseason with mottled red over color on an attractive orange ground color, semi-clingstone fruit with a juicy, melting texture and sweet, mild flavor, firm fruit that retain their firmness well and trees with regular, heavy production of large fruit.

6 Drawing Sheets

Latin name of genus and species of the plant claimed: *Prunus persica* L.
Cultivar name: 'NJF18'.

BACKGROUND OF THE INVENTION

The present invention relates to a new and distinct variety of peach tree named 'NJF18'. Our new tree resulted from crossing 'H15-20-90258' (unpatented) as the seed parent with 'A34-160-782118' (unpatented) as the pollen parent. The new variety differs from seed parent 'H15-20-90258' (unpatented) in that the new variety has flat fruit while the seed parent has round fruit. The new variety differs from pollen parent A34-160-782118' (unpatented) in that the new variety has pubescent fruit while the pollen parent has glabrous fruit. The resulting tree was selected when growing in a cultivated area as the $72^{nd}$ tree in the $10^{th}$ row of Block L at the Rutgers Fruit Research and Extension Center in Cream Ridge, N.J.

BRIEF SUMMARY OF THE INVENTION

The 'NJF18' variety is distinguished from other peach varieties due to the following unique combination of characteristics:

- Flat fruit shape.
- Fruit with mottled red over color on an attractive orange ground color.
- Good productivity of large fruit,
- Sweet, mild flavor.
- Melting flesh texture
- Very firm fruit that retain their firmness well.

The variety was asexually reproduced at the Rutgers Fruit Research and Extension Center in Cream Ridge, N.J. Asexual reproduction of this new variety by budding onto 'Lovell' rootstock (unpatented) for several generations shows that the foregoing characteristics are so reproduced.

The following detailed description concerns the original tree, 'NJF18'. The original tree and asexual progeny have been observed growing in a cultivated area in Cream Ridge, N.J. Certain characteristics of this variety, such as growth and color, may change with changing environmental conditions (such as, light, temperature, moisture, nutrient availability) or other favors. Color descriptions and other terminology are used in accordance with their ordinary dictionary descriptions, unless the context clearly indicates otherwise. Color designations are made with reference to The Royal Horticultural Society (RHS) Colour Chart.

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

DETAILED BOTANICAL DESCRIPTION

Figure 1:
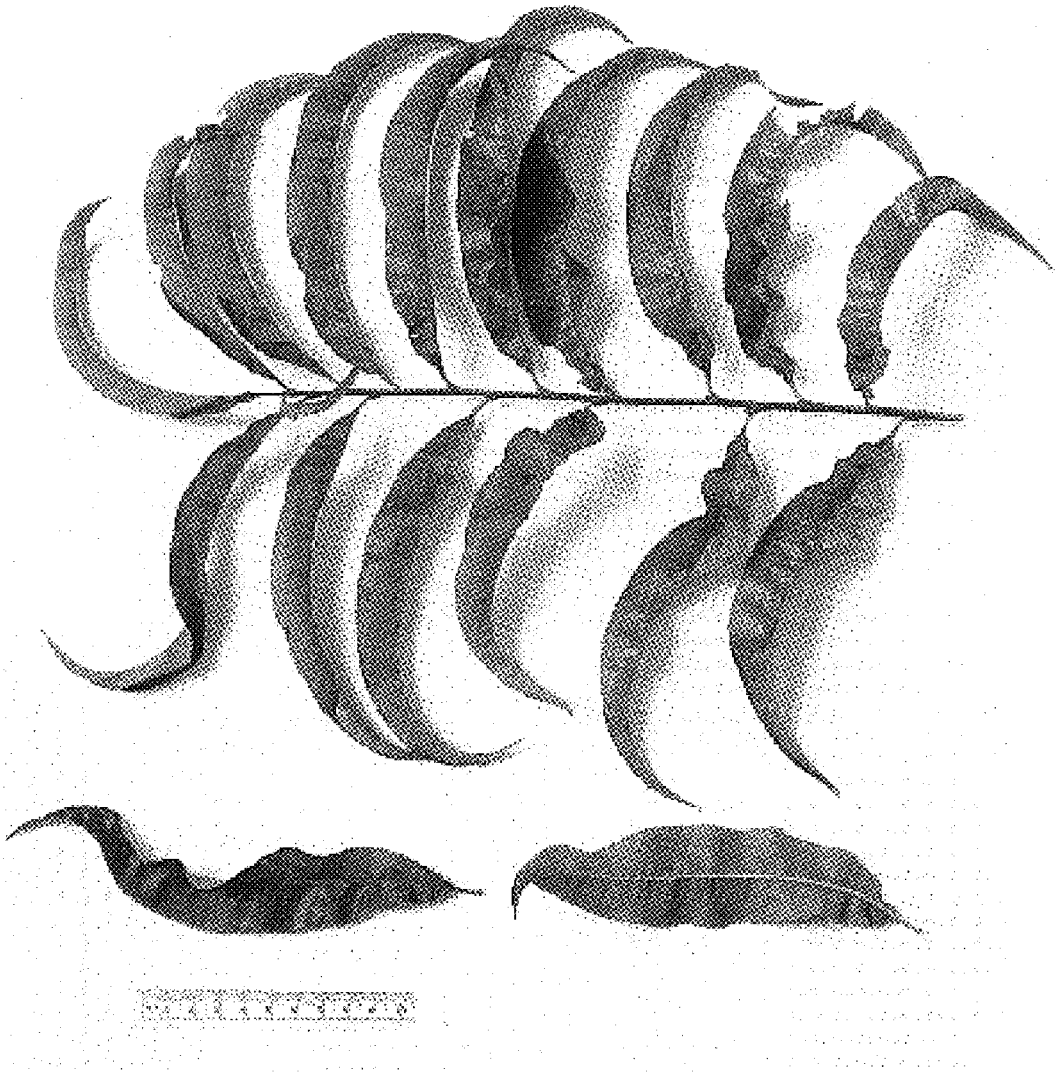
FIG. 1 is a color photograph taken on Aug. 29, 2005 of a characteristic twig of 'NJF18' in late summer bearing typical crinkled and slightly wavy leaves of the mature foliage.
Figure 2:
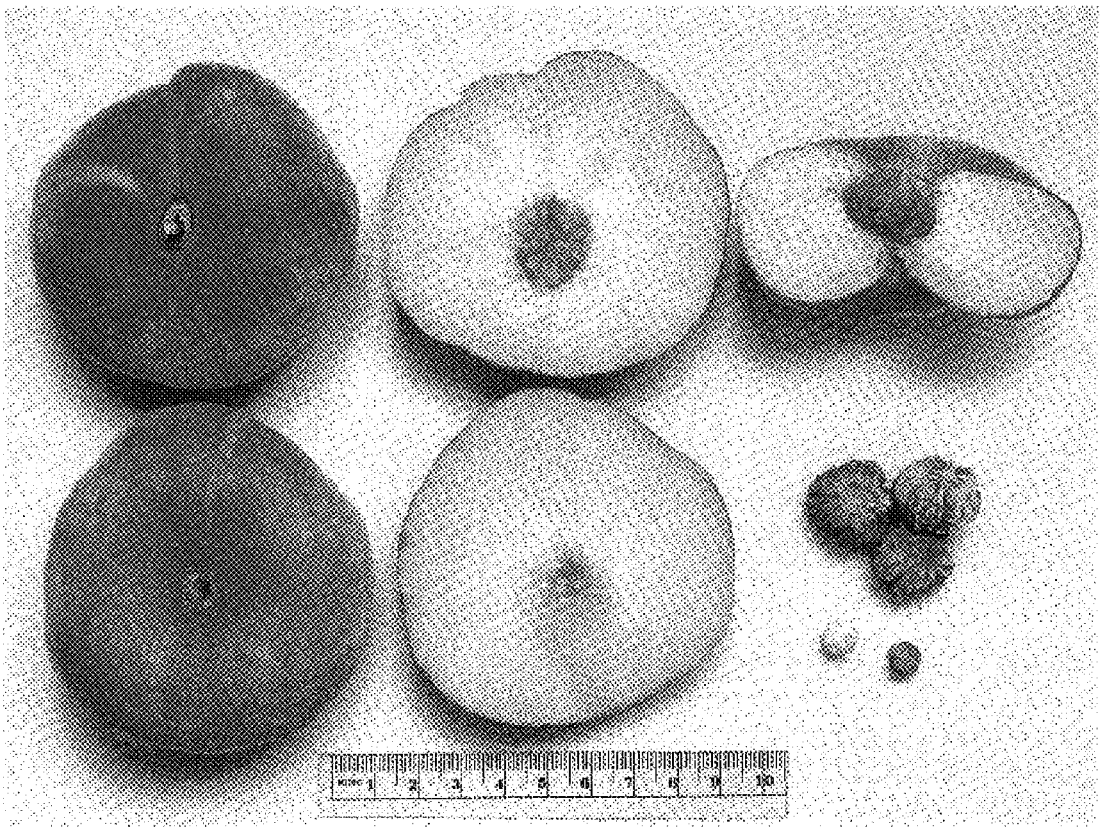
FIG. 2 is a color photograph of mature fruit of 'NJF18' and stones harvested in Cream Ridge, N.J. on Aug. 9, 2005. Whole fruit are presented in two positions and a cross section to show that the pericarp adheres partially to the pit when the fruit is mature. The stones illustrate the low to medium height and medium width of the dorsal ridge and the pit grooves on the surface of the stone.
Figure 3:
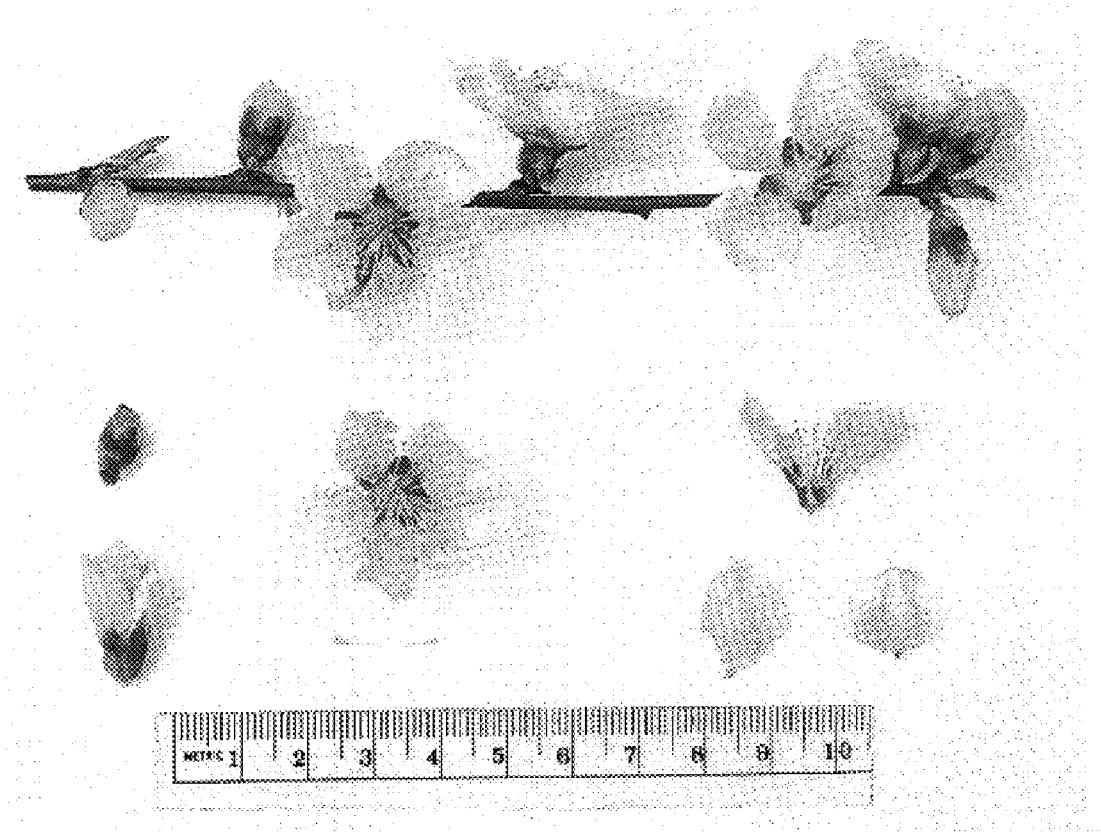
FIG. 3 is a color photograph of a characteristic twig that illustrates the typical flower buds and showy flowers of 'NJF18' observed on a tree in Cream Ridge, N.J. on Apr. 9, 2006.
Figure 4:
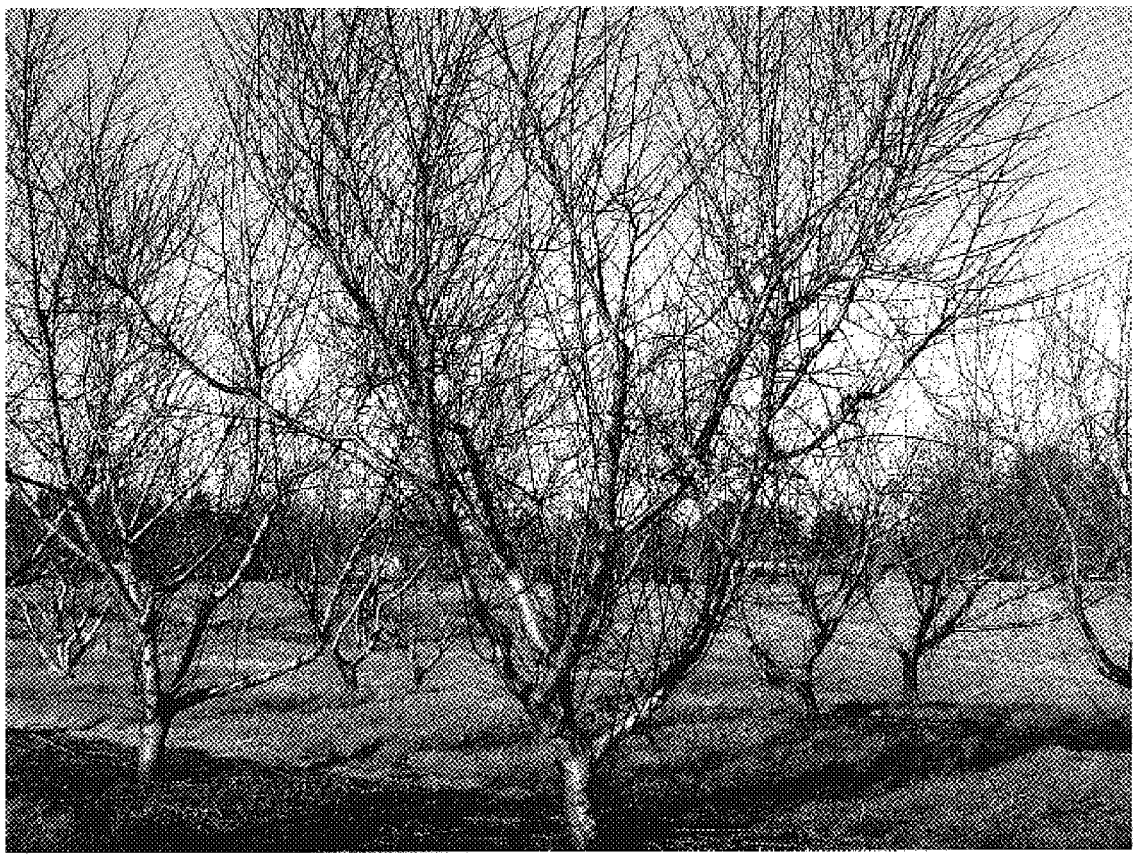
FIG. 4 is a color photograph of a tree of 'NJF18' in winter that illustrates the slightly upright growth habit of a tree in Cream Ridge, N.J. on Jan. 2, 2007.
Figure 5:
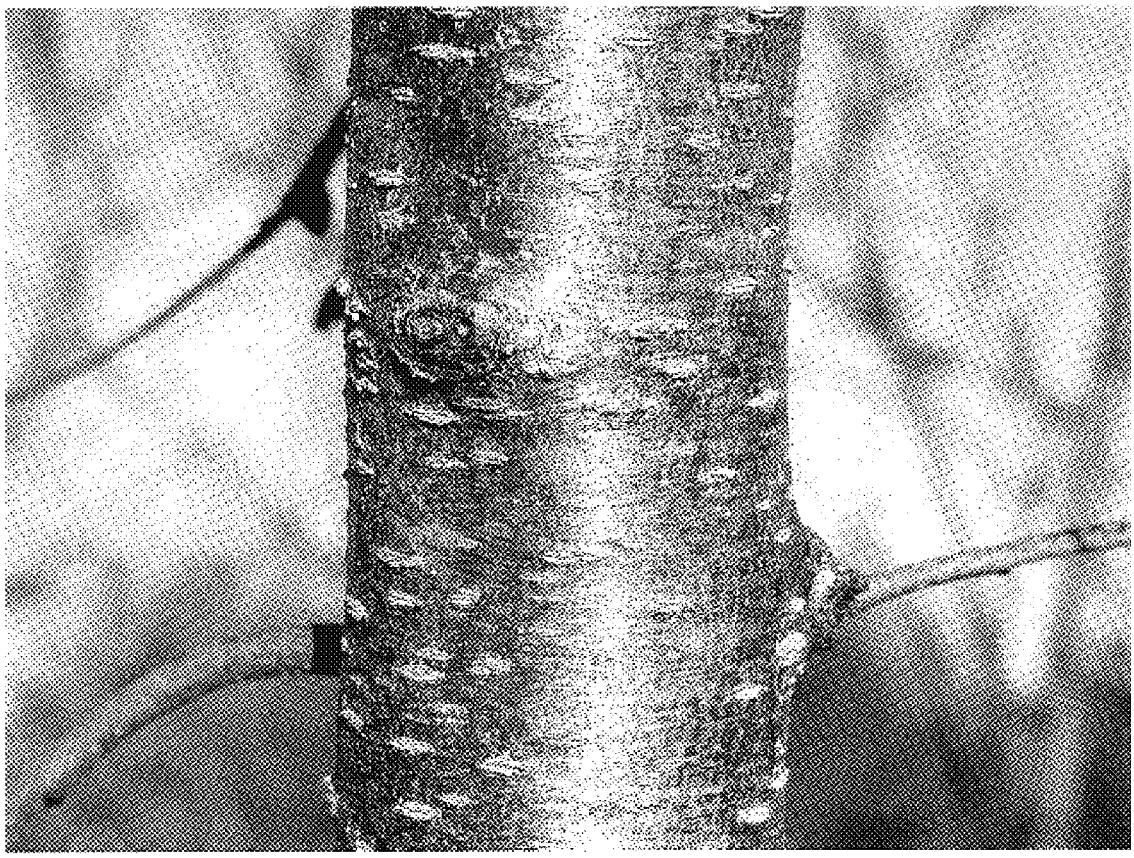
FIG. 5 is a color photograph taken on Jan. 2, 2007 of immature bark of 'NJF18' that illustrates color and the low density of elliptical lenticels on the immature bark.
Figure 6:
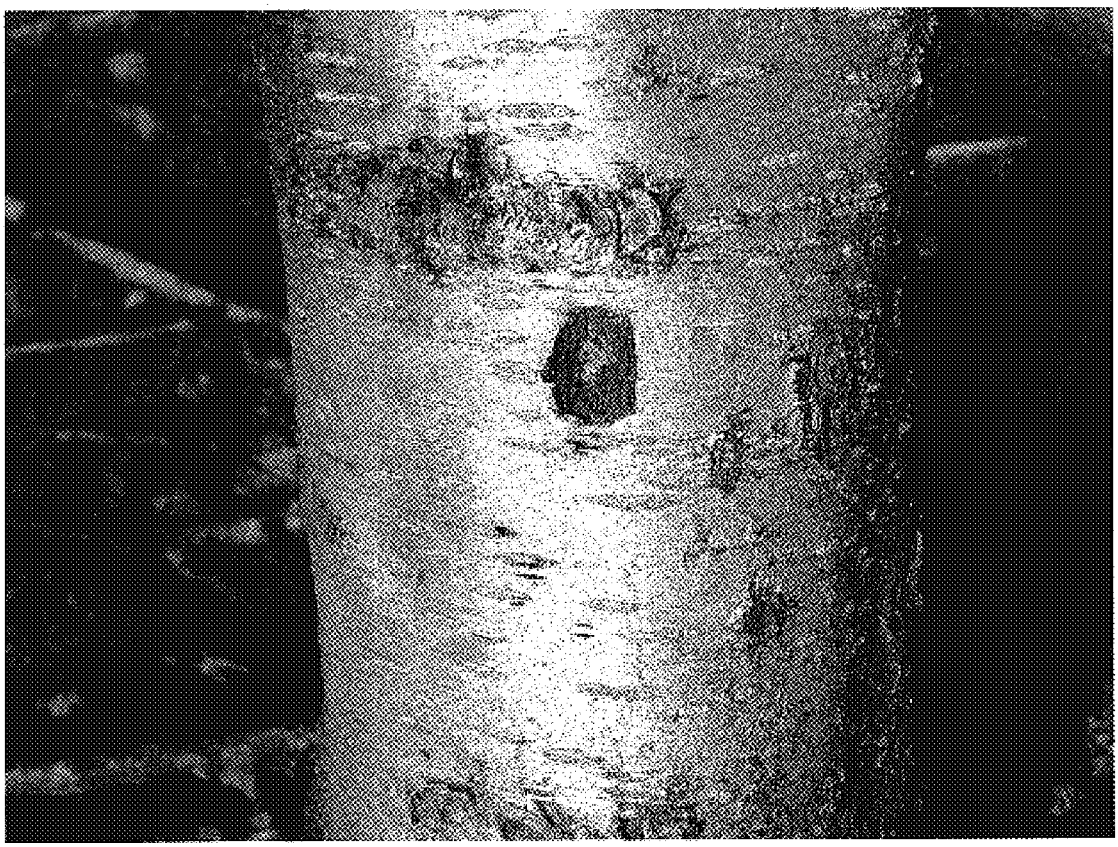
FIG. 6 is a color photograph taken on Jan. 2, 2007 of mature bark of 'NJF18' that illustrates the smooth to slightly rough texture of the mature bark.

The following detailed description of the 'NJF18' variety is based on observations of an asexually reproduced tree. The observed tree was five years of age and growing on 'Lovell' seedling rootstock (unpatented) in Research Block C at the Rutgers Fruit Research and Extension Center in Cream Ridge, N.J.

Latin name of genus and species: *Prunus persica* L.
Parentage:

| | |
|---|---|
| Seed parent: | 'H15-20-90258' |
| Pollen parent: | 'A34-160-782118' |

Tree:

| | |
|---|---|
| Vigor: | Above average. |
| Plant hardiness zone: | Growth of plants has only been observed in zone 6b. |
| Dormant flower bud cold tolerance: | At least to −16° C. |
| Overall shape: | Slightly upright with a rounded canopy. |
| Height: | Above average as compared to other peach cultivars. For example, measurement of a typical grafted tree on 'Lovell' seedling rootstock (unpatented) at five years after planting shows an average height of 4 meters when grown in Cream Ridge, New Jersey. |
| Width: | Slightly above average as compared to other peach cultivars. For example, measurement of a typical grafted tree on 'Lovell' seedling rootstock (unpatented) at five years after planting shows an average width of 4 meters when grown in Cream Ridge, New Jersey. |
| Caliper: | Five year old tree is 37.5 cm in circumference measured at 20 cm from the ground. |

Trunk and branches:

| | |
|---|---|
| Trunk bark texture: | Smooth to slightly rough. |
| Trunk bark color: | Grey (RHS 201d). |
| Primary branches: | Branches that are approximately 15 cm in circumference have a greyed-orange (RHS 174a) under color, overlaid with grey (RHS 201d). |
| Lenticels: | Low density, approximately 1 per square cm; narrowly elliptical in shape; typical examples of which measured 4.6 mm in length; greyed-orange (RHS 164c) in color, bordered with greyed-orange (RHS 164b). |
| Branch pubescence: | None. |
| New growth bark: | Color greyed-purple (RHS 183a) in sun; color yellow-green (RHS 152d). |

-continued

| | |
|---|---|
| Internodes: | Length 23 mm to 28 mm, averaging 26.6 mm on a one-year shoot. |

Leaves:

| | |
|---|---|
| Texture: | Glabrous. |
| Sheen: | Young leaves semi-glossy with a flat finish on the underside. |
| Length: | About 152 mm to 195 mm, averaging about 173 mm including the petiole. |
| Width: | About 42 mm to 47 mm, averaging about 40 mm. |
| Petiole: | About 9.4 mm long and about 1.3 mm in diameter. |
| Margin: | Serrulate. |
| Margin undulation: | Crinkled and slightly wavy. |
| Form: | Lanceolate. |
| Apex: | Sharply acute, curved downward. |
| Base: | Broadly acute. |
| Venation: | Pinnate. |
| Glands: | |
| Number: | Typically between 1 to 5, averaging about 3. |
| Position: | Located on the petiole and leaf margin. |
| Size: | Length averaging 1.2 mm and width averaging 0.9 mm. |
| Form: | Reniform. |
| Stipules: | None observed on mature leaves. |
| Leaf Color: | |
| Upper leaf surface: | Yellow-green (between RHS 147a to RHS 147b). |
| Lower leaf surface: | Yellow-green (RHS 147b). |
| Vein: | Yellow-green (RHS 145c). |
| Pubescence: | None. |

Flowers:

| | |
|---|---|
| Size: | Medium size, about 27 to 33 mm across, averaging about 31.3 mm. |
| Color: | |
| Dormant bud: | Grey (RHS 201a) to greyed-green (RHS 197c). |
| Pink stage bud: | Red (55c). |
| Open flower: | Red (RHS 56b) becoming red-purple (RHS 62b) at petal fall. |
| Petals: | Typically five petals per flower; nearly round shape with a wavy to slightly crinkled margin; about 17.1 mm long and 15.4 mm wide. |
| Petal apex: | Obtuse. |
| Petal base: | Abruptly acuminate. |
| Stamens: | |
| Number: | Variable, typical range 37 to 43, averaging about 40. |
| Length: | Between 9 mm to 10 mm, averaging 9.5 mm. |
| Filament color: | Yellow (RHS 2d). |
| Anther color: | Greyed-orange (RHS 163b). |
| Pistil: | |
| Number: | One. |
| Size: | Length between 13 and 15 mm, averaging about 14.3 mm. |
| Pistil color: | Yellow-green (RHS 145a). |
| Ovary: | Moderately pubescent, and oblate in shape. |
| Sepals: | |
| Number: | Typically five. |
| Pubescence: | Light. |
| Color: | Yellow-green (RHS 144d) with a greyed-orange (RHS 176a) over color. |
| Shape: | Triangular, with a rounded apex. |
| Size: | Length averaging 4 mm, width averaging 3.3 mm. |
| Nectar cup color: | Greyed-orange (RHS 167a). |

-continued

| | |
|---|---|
| Pollen: | None. |
| Fragrance: | Very slight. |
| Bloom season: | Onset of bloom on Apr. 8, 2006; full bloom on Apr. 11, 2006. |

Fruit:

| | |
|---|---|
| Size: | Large for a flat peach, about 4.2 cm long, 7.9 cm wide parallel to the suture, and 8.1 cm wide perpendicular to the suture. |
| Typical weight: | 169.4 g. |
| Form: | |
| Longitudinal section: | Oblate. |
| Traverse section: | Triangular. |
| Suture: | Shallow. |
| Ventral surface: | Varies between slightly lipped to lipped. |
| Base: | Truncated and indented. |
| Apex: | Depressed; between 4.4 to about 15.8 mm in diameter, with an average of 8.7 mm. |
| Stem: | Average length of 5.3 mm and an average diameter of 9.3 mm. |
| Skin: | |
| Thickness: | Average. |
| Surface: | Regular with moderate pubescence. |
| Tenacity: | Average. |
| Astringency: | Little to none. |
| Tendency to crack: | Low. |
| Color: | Mottled red (between RHS 53a to RHS 46a) over color; ground color orange (RHS 24b). |
| Fruit Properties: | |
| Flesh color: | Yellow-orange (between RHS 21b and RHS 21c, becoming RHS 20b near the stone). |
| Flesh adhesion: | Semi-clingstone. |
| Juice: | Moderate. |
| Texture: | Melting. |
| Fibers: | Not noticeable. |
| Ripens: | Between July 21 and August 2 at Cream Ridge, New Jersey. |
| Flavor: | Sweet, mild. |
| Soluble solids: | 12.3%. |
| Aroma: | Moderate. |
| Eating quality: | Very good. |

-continued

| | |
|---|---|
| Keeping quality: | Average. Has held its flavor and firmness for at least 10 days in cold storage at 1° C. to 4° C. |
| Shipping quality: | Average. |
| Usage: | Dessert. |
| Market: | Local and long distance. |
| Productivity: | Above average for a flat peach. Trees have produced a crop in 6 out of 7 years and a full crop in 5 out of 7 years at Cream Ridge, New Jersey. |

Stone:

| | |
|---|---|
| Type: | Semi-clingstone. |
| Form: | Oblate. |
| Base: | Very broad. |
| Apex: | Very broad. |
| Surface: | Pit grooves. |
| Ventral suture: | Low and deeply grooved on both sides. |
| Dorsal ridge: | Low to medium height, medium width. |
| External Color: | Greyed-orange (between RHS 165c and RHS 165d). |
| Internal color when cracked: | Greyed-orange (RHS 165d). |
| Cavity surface color: | Greyed-orange (RHS 165d). |
| Average stone weight: | Dry weight 2.3 g. |
| Average stone wall thickness: | Variable, between 2.1 and 7.2 mm. |
| Size: | Averages about 13.8 mm long, 21.0 mm wide parallel to the dorsal ridge, and 19.2 mm wide perpendicular to the dorsal ridge. |
| Tendency to split: | Very low. |
| Kernel: | |
| Form: | Irregular. |
| Skin color: | Greyed-orange (RHS 164a). |
| Vein color: | Greyed-orange (RHS 165b). |
| Viable: | No. |
| Size: | Highly variable; forms only rudimentary seed. |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *